United States Patent
Bishop et al.

(10) Patent No.: US 7,094,847 B2
(45) Date of Patent: Aug. 22, 2006

(54) METALLOCENE COMPOUNDS AND USE THEREOF IN CATALYSTS FOR THE POLYMERIZATION OF OLEFINS

(75) Inventors: Clyde E. Bishop, Hockessin, DE (US); Robert L. Jones, Jr., Elkton, MD (US); Krishna Raman, Wilmington, DE (US); Vu Anh Dang, Bear, DE (US); Lin-Chen Yu, Hockessin, DE (US); Luigi Resconi, Ferrara (IT); Tiziano Dall'Occo, Ferrara (IT); Maurizio Galimberti, Milan (IT)

(73) Assignee: Basell Technology Company B.V., Hoofddorp (NL)

( * ) Notice: Subject to any disclaimer, the term of this patent is extended or adjusted under 35 U.S.C. 154(b) by 633 days.

(21) Appl. No.: 09/823,393

(22) Filed: Mar. 30, 2001

(65) Prior Publication Data

US 2001/0012877 A1   Aug. 9, 2001

Related U.S. Application Data

(62) Division of application No. 08/417,735, filed on Apr. 5, 1995, now Pat. No. 6,211,108.

(30) Foreign Application Priority Data

Apr. 6, 1994 (IT) .............................. MI94A0645

(51) Int. Cl.
  *C08F 4/42* (2006.01)
(52) U.S. Cl. .................. 526/160; 526/348; 526/351; 526/352; 526/335; 526/336; 526/943; 502/103; 502/152

(58) Field of Classification Search ................ 526/160, 526/127, 943, 351, 348, 352, 335, 336; 502/152, 502/103; 556/11, 28, 53
See application file for complete search history.

(56) References Cited

U.S. PATENT DOCUMENTS 5,296,433 A * 3/1994 Siedle et al. ................. 502/117
5,441,920 A * 8/1995 Welborn, Jr. ................. 502/103

FOREIGN PATENT DOCUMENTS

| EP | 0 035 242 A1 | 9/1981 |
|----|----|----|
| EP | 0 129 368 A1 | 12/1984 |
| EP | 0 351 392 A2 | 1/1990 |
| EP | 0 407 870 A2 | 1/1991 |
| EP | 0 501 370 A1 | 9/1992 |
| EP | 0 501 370 A1 | 7/1994 |
| EP | 0 604 908 A2 | 7/1994 |
| EP | 0 632 066 A1 | 1/1995 |

OTHER PUBLICATIONS

J. Am. Chem. Soc., 82, 2498 (1960).
J. Am. Chem. Soc., 83, 5003 (1961).
J. Chem. Soc. Chem. Comm., 935 (1973).

* cited by examiner

*Primary Examiner*—Ling-Sui Choi
(74) *Attorney, Agent, or Firm*—Bryan Cave LLP

(57) ABSTRACT

A class of bridged or unbridged metallocene compounds is disclosed, wherein the cyclopentadienyl ligands have two or four adjacent substituents forming one or two alkylenic cycles of from 4 to 8 carbon atoms.

These metallocenes are useful as catalyst components for the polymerization of olefins, particularly for the (co)polymerization of ethylene and for the polymerization of propylene.

10 Claims, No Drawings

METALLOCENE COMPOUNDS AND USE THEREOF IN CATALYSTS FOR THE POLYMERIZATION OF OLEFINS

This is a divisional of U.S. application Ser. No. 08/417,735, filed, Apr. 5, 1995 now U.S. Pat. No. 6,211,108.

BACKGROUND OF THE INVENTION

1. Field of the Invention

The present invention relates to a class of metallocene compounds, to a catalyst for the polimerization of olefins comprising said metallocenes and to processes for the polimerization of olefins carried out in the presence of said catalyst.

The invention also relates to processes for the preparation of the ligands of said metallocenes, as well as to a class of novel bridged ligands.

2. Description of the Prior Art

Metallocene compounds are known which are active as catalyst components in the olefin polymerization reactions.

European patent application EP-A-35 242, for instance, discloses a process for the polymerization of ethylene and propylene in the presence of a catalyst system comprising (a) a cyclopentadienyl compound of a transition metal and (b) an alumoxane.

European patent application EP-A-129 368 discloses a catalyst system for the polymerization of olefins comprising (a) a mono-, bi- or tri-cyclopentadienyl coordination complex with a transition metal and (b) an alumoxane. With this catalyst it is possible to prepare polyolefins of controlled molecular weight.

European patent application EP-A-351 392 discloses a catalyst, which can be used in the preparation of syndiotactic polyolefins, comprising a metallocene compound with two cyclopentadienyl based rings linked with a bridging group in which one of the two cyclopentadiene rings is substituted differently from the other. The preferred compound indicated is isopropylidene(fluorenyl)(cyclopentadienyl) hafnium dichloride.

EP-A-604 908 discloses a class of bis-fluorenyl compounds bridged with a one-atom-bridge. These metallocenes are useful as catalyst components for the polymerization of olefins and, expecially, for the preparation of high molecular weight atactic polypropylene.

SUMMARY OF THE INVENTION

New metallocene compounds have now been found which can be advantageously used as catalyst components in the polymerization reactions of olefins.

An object of the present invention consists of a new metallocene compound of formula (I)

$$(YR_p)_q(Cp)(Cp')MX_2 \quad (I)$$

wherein Cp is a group selected from those of formula (II) and (III):

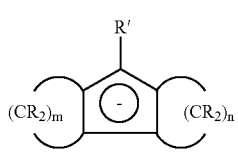
(II)

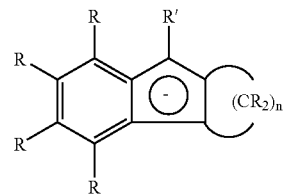
(III)

wherein m and n, same or different from each other, are integer comprised between 2 and 6 and, preferably, comprised between 3 and 5;

Cp' is a group selected from those of formula (II), (III) e (IV):

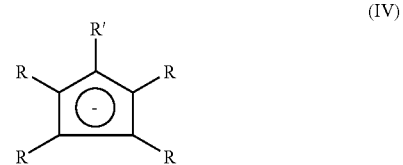
(IV)

wherein $(YR_p)_q$ is a divalent group which bridges the two groups Cp and Cp', Y being selected indifferently from C, Si, Ge, N and P; p is 1 when Y is N or P, and is 2 when Y is C, Si or Ge;

q can be 0, 1, 2 or 3;

M is a transition metal selected from Ti, Zr or Hf;

the substituents X, same or different from each other, are halogen atoms, —OH, —SH, R, —OR, —SR, —NR$_2$ or —PR$_2$;

the substituents R, same or different from each other, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals, optionally containing Si or Ge atoms and, additionally, two adjacent R substituents on Cp or Cp' may form a $C_5$–$C_8$ cycle and, further, two R substituents of the same YR$_2$ group or of two adjacent YR$_2$ groups may form a ring comprising from 3 to 8 atoms;

when q=0, the R' substituents are defined as the R substituents while, when q=1, 2 or 3, the two R' substituents of the groups Cp and Cp' together form the divalent group $(YR_p)_q$.

Another object of the present invention is a process for the preparation of a cyclopentadienylic compound of formula (II), which comprises reacting a cycloalkene of formula (V) with a cycloalkene derivative of formula (VI) to obtain a cyclopentenone of formula (VII), wherein n, m and R have the meaning given, and X is OH, OR, O(CO)R, Cl or Br, in accordance with the reaction scheme below:

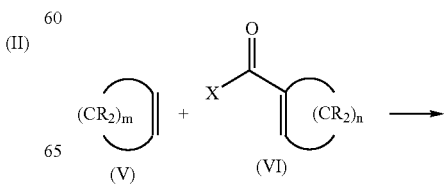

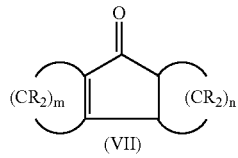

(VII)

Still another object of the present invention is a process for the preparation of a cyclopentadienylic compound of formula (III), which comprises reacting a cycloalkene of formula (V') with a benzene derivative of formula (VIII) to obtain a compound of formula (IX), wherein n, m, R and X have the meaning given, in accordance with the reaction scheme below:

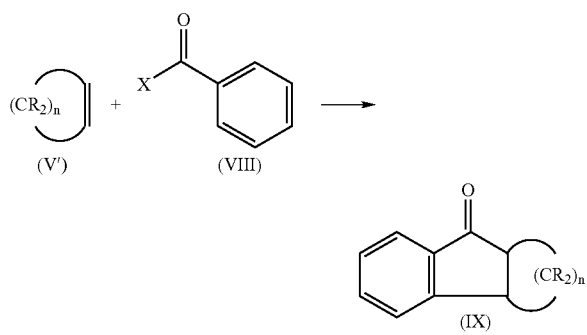

Yet another object of the present invention is a cyclopentadiene ligand of formula (XI):

$$(YR_p)_q(CP)(Cp')$$ (XI)

wherein Cp, Cp', $(YR_p)_q$, Y, R, p and q have the meaning given.

A further object of the present invention is a catalyst for the polymerization of olefins comprising the product of the reaction between:

(A) a metallocene compound of formula (I), optionally as a reaction product with a organo-aluminium of formula $AlR^4{}_3$ or $Al_2R^4{}_6$, in which the substituents $R^4$, same or different from each other are $R^1$ or halogen, and (B) an aluminoxane, optionally in admixture with a organo-aluminium compound of formula $AlR^4{}_3$ or $Al_2R^4{}_6$, in which the substituents $R^4$, same or different from each other, are defined as above or one or more compounds capable of forming a alkyl metallocene cation.

Still a further object of the invention consists of a process for the polymerization of olefins comprising the polymerization reaction of at least one olefinic monomer in the presence of the above described catalyst.

Yet a further object of the present invention is a process for the oligomerization of propylene carried out in the presence of the above described catalyst.

DESCRIPTION OF THE PREFERRED EMBODIMENTS

The preferred R substituents are hydrogen, $C_1$–$C_{10}$ alkyl radicals, more preferably $C_1$–$C_3$, $C_3$–$C_{10}$ cycloalkyl radicals, more preferably $C_3$–$C_6$, $C_2$–$C_{10}$ alkenyl radicals, more preferably $C_2$–$C_3$, $C_6$–$C_{10}$ aryl radicals $C_7$–$C_{10}$ alkaryl radicals or $C_7$–$C_{10}$ aralkyl radicals. The alkyl radicals may be straight chain or branched in addition to cyclic.

The divalent group $(YR_p)_q$ is preferably selected from $CR_2$, $SiR_2$, $GeR_2$, NR, PR and $(CR_2)_2$. More preferably is a group selected from $Si(CH_3)_2$, $CH_2$, $(CH_2)_2$ and $C(CH_3)_2$.

The preferred transition metal M is Zr.

The X substituents are preferably halogen atoms or R groups. More preferably are chlorine or a methyl radical.

Non limitative examples of ligands of formula (II) according to the invention are: octahydrofluorene, 9-methyl-octahydrofluorene, bis(cyclotrimethylene)cyclopentadiene.

Non limitative examples of ligand of formula (III) according to the invention are: tetrahydrofluorene, 1,2-cyclohexamethylene-indene.

Non limitative examples of ligand of formula (IV) according to the invention are: cyclopentadienyl, indenyl, tetrahydroindenyl.

A particular class of metallocene according to the invention is those compounds of formula (I) in which q=0, and that is those in which the Cp and Cp' groups are not linked to each other by a bridge.

Non limitative examples of the above mentioned class of metallocenes are:
bis(1, 2-cyclotetramethyleneinden-yl)titanium dichloride,
bis(1,2-cyclotetramethyleneinden-1-yl)zirconium dichloride,
bis(1,2-cyclotetramethyleneinden-1-yl) hafnium dichloride,
bis(1,2-cyclotetramethyleneinden-1-yl)titanium dimethyl,
bis(1,2-cyclotetramethyleneinden-1-yl)zirconium dimethyl,
bis(1,2-cyclotetramethyleneinden-1-yl) hafnium dimethyl,
bis(octahydrofluorenyl)titanium dichloride,
bis(octahydrofluorenyl)zirconium dichloride,
bis(octahydrofluorenyl)hafnium dichloride,
bis(octahydrofluorenyl)titanium dimethyl,
bis(octahydrofluorenyl)zirconium dimethyl,
bis(octahydrofluorenyl)hafnium dimethyl,
(cyclopentadienyl)(1,2-cyclotetramethyleneinden-1-yl)titanium dichloride,
(cyclopentadienyl)(1,2-cyclotetramethyleneinden-1-yl)zirconium dichloride,
(cyclopentadienyl)(1,2-cyclotetramethyleneinden-1-yl) hafnium dichloride,
(cyclopentadienyl)(1,2-cyclotetramethyleneinden-1-yl)titanium dimethyl,
(cyclopentadienyl)(1,2-cyclotetramethyleneinden-1-yl)zirconium dimethyl,
(cyclopentadienyl)(1,2-cyclotetramethyleneinden-1-yl) hafnium dimethyl,
(cyclopentadienyl)(octahydrofluorenyl)titanium dichloride,
(cyclopentadienyl)(octahydrofluorenyl)zirconium dichloride,
(cyclopentadienyl)(octahydrofluorenyl)hafnium dichloride,
(cyclopentadienyl)(octahydrofluorenyl)titanium dimethyl,
(cyclopentadienyl)(octahydrofluorenyl)zirconium dimethyl,
(cyclopentadienyl)(octahydrofluorenyl)hafnium dimethyl.

Another particular class of metallocenes according to the invention is those compounds of formula (I) in which q is different from 0, and the groups Cp and Cp', preferably same as each other, are selected from those of formula (II) and (III). Preferably, the divalent group $(YR_p)_q$ is a $Si(CH_3)_2$ group.

Non limitative examples of above cited metallocenes are:
dimethylsilanediylbis(2,3-cyclotetramethyleneinden-1-yl) titanium dichloride,
dimethylsilanediylbis(2,3-cyclotetramethyleneinden-1-yl) zirconium dichloride, dimethylsilanediylbis(2,3-cyclotetramethyleneinden-1-yl) hafnium dichloride,
dimethylsilanediylbis(2,3-cyclotetramethyleneinden-1-yl) titanium dimethyl,
dimethylsilanediylbis(2,3-cyclotetramethyleneinden-1-yl) zirconium dimethyl,
dimethylsilanediylbis(2,3-cyclotetramethyleneinden-1-yl) hafnium dimethyl,
diphenylsilanediylbis(2,3-cyclotetramethyleneinden-1-yl)titanium dichloride,
diphenylsilanediylbis(2,3-cyclotetramethyleneinden-1-yl) zirconium dichloride,
diphenylsilanediylbis(2,3-cyclotetramethyleneinden-1-yl) hafnium dichloride,
diphenylsilanediylbis(2,3-cyclotetramethyleneinden-1-yl)titanium dimethyl,
diphenylsilanediylbis(2,3-cyclotetramethyleneinden-1-yl) zirconium dimethyl,
diphenylsilanediylbis(2,3-cyclotetramethyleneinden-1-yl) hafnium dimethyl,
isopropylidenebis(2,3-cyclotetramethyleneinden-1-yl)titanium dichloride,
isopropylidenebis(2,3-cyclotetramethyleneinden-1-yl)zirconium dichloride,
isopropylidenebis(2,3-cyclotetramethyleneinden-1-yl) hafnium dichloride,
isopropylidenebis(2,3-cyclotetramethyleneinden-1-yl)titanium dimethyl,
isopropylidenebis(2,3-cyclotetramethyleneinden-1-yl)zirconium dimethyl,
isopropylidenebis(2,3-cyclotetramethyleneinden-1-yl) hafnium dimethyl,
dimethylgermanedylbis(2,3-cyclotetramethyleneinden-1-yl) titanium dichloride,
dimethylgermanedylbis(2, 3-cyclotetramethyleneinden-1-yl)zirconium dichloride,
dimethylgermanedylbis(2,3-cyclotetramethyleneinden-1-yl) hafnium dichloride,
dimethylgermanedylbis(2,3-cyclotetramethyleneinden-1-yl) titanium dimethyl,
dimethylgermanedylbis(2,3-cyclotetramethyleneinden-1-yl) zirconium dimethyl,
dimethylgermanedylbis(2,3-cyclotetramethyleneinden-1-yl) hafnium dimethyl,
dimethylsilanediylbis(octahydrofluorenyl)titanium dichloride,
dimethylsilanediylbis(octahydrofluorenyl)zirconium dichloride,
dimethylsilanediylbis(octahydrofluorenyl)hafnium dichloride,
dimethylsilanediylbis(octahydrofluorenyl)titanium dimethyl,
dimethylsilanediylbis(octahydrofluorenyl)zirconium dimethyl,
dimethylsilanediylbis(octahydrofluorenyl)hafnium dimethyl.

Yet another particular class of metallocenes according to the invention is those compounds of formula (I) in which q=1 and the group Cp' is a non-substituted cyclopentadienyl group. Preferably, the divalent group $(YR_p)_q$ is a group $>C(CH_3)_2$.

Non limitative examples of the above cited class of metallocenes are:
isopropylidene(cyclopentadienyl)(2,3-cyclotetramethyleneinden-1-yl)titanium dichloride,
isopropylidene(cyclopentadienyl)(2,3-cyclotetramethyleneinden-1-yl)zirconium dichloride,
isopropylidene(cyclopentadienyl)(2,3-cyclotetramethyleneinden-1-yl)hafnium dichloride,
isopropylidene(cyclopentadienyl)(2,3-cyclotetramethyleneinden-1-yl)titanium dimethyl,
isopropylidene(cyclopentadienyl)(2,3-cyclotetramethyleneinden-1-yl) zirconium dimethyl,
isopropylidene(cyclopentadienyl)(2,3-cyclotetramethyleneinden-1-yl)hafnium dimethyl,
isopropylidene(cyclopentadienyl)(octahydrofluorenyl)titanium dichloride,
isopropylidene(cyclopentadienyl)(octahydrofluorenyl)zirconium dichloride,
isopropylidene(cyclopentadienyl)(octahydrofluorenyl) hafnium dichloride,
isopropylidene(cyclopentadienyl)(octahydrofluorenyl)titanium dimethyl,
isopropylidene(cyclopentadienyl)(octahydrofluorenyl)zirconium dimethyl,
isopropylidene(cyclopentadienyl)(octahydrofluorenyl) hafnium dimethyl.

Both the above indicated reactions for the preparation of a cyclopentadienylic compound of formula (II) or (III) are conducted in an acid medium. Suitable acid compounds which can be used, alone or in combination, are:
   mineral acids, such as polyphosphoric acid, phosphoric acid, sulfuric acid, hydrochloric acid, hydrobromic acid;
   organic acids and peracids, such as formic acid, acetic acid, trifluoroacetic acid, fluorosulfonic acid, methanesulfonic acid, p-toluenesulfonic acid;
   metal cations, such as silver tetrafluoroborate;
   trimethylsilyl iodide;
   phosphorus pentaoxide;

polyphosphoric acid being the preferred.

The above said reactions can be conducted in a solvent such as methanol, ethanol, acetic anhydride, methylene chloride, carbon tetrachloride, 1,2-dichloroethane, benzene, toluene.

The reaction temperature is generally comprised in the range of −78° C. to 350° C., preferably of from 0° C. to 200° C. and, more preferably, of 65° C. to 100° C.

The reaction time is generally comprised in the range of 2 minutes to 24 hours and, preferably, of 1 to 4 hours.

The cycloalkenes (V) are commercially obtainable, while the 1-cycloalkene derivatives (VI) and the benzene derivatives (VIII) which either are commercially obtainable or can be prepared by known methods.

The cyclopentenones (VII) and the compounds (IX) can successively be converted to cyclopentadienyl compounds of, respectively, formula (II) and (III) by means of different methods.

For example, the cyclopentenone (VII) and the compound (IX) can be first reduced and then dehydrated to yield the cyclopentadiene (II).

Reducing agents suitable for use in the reduction step are, for example, diisopropylaluminum hydride, diisobutylaluminum hydride, lithium aluminum hydride, aluminum hydride, 9-BBN.

The dehydration step may be performed in the presence of an acid, $SOCl_2$, $POCl_3$.

The conditions for these reaction are reported in J. Am. Chem. Soc., 82, 2498 (1960), and ibid. 83, 5003 (1961).

Alternatively, the cyclopentenone (VII) and the compound (IX) can be directly transformed into the cyclopentadiene (II) by reaction with metallic Zn and trimethylsilyl chloride, as described in J. Chem. Soc. Chem. Comm., 935 (1973).

According to another method, the cyclopentenone (VII) and the compound (IX), can be reacted with a substituted or unsubstituted p-toluensulfonhydrazide of formula (X)

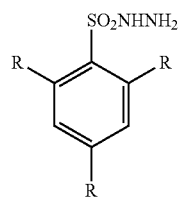

(X)

The reaction is carried out in a solvent such as, for example, alcohols, tetrahydrofurane (THF), ethers, benzene, toluene, in the presence or absence of acids, to yield a tosylhydrazone. The water formed during the above reaction may be removed.

The thus obtained tosylhydrazone is thereafter reacted with a base to yield the desired products. The reaction is carried out in a solvent such as, for example, hexane, pentane, diethyl ether, N,N,N',N'-tetramethyl-ethylenediamine. Bases suitable for use in the above reaction are, for instance, methyllithium, n-buthyllithium, s-buthyllithium, t-buthyllithium, lithium, sodium or potassium dialkylamide, potassium t-butoxide, lithium, sodium or potassium hexamethyldisilylazide, sodium hydride, potassium hydride.

The preparation of the bridged ligands of the metallocene compounds of formula (I) wherein q is different from 0 and the group Cp is the same as the group Cp', can be carried out by first reacting a compound of formula (II) or (III) with a compound able to form a delocalized anion on the cyclopentadienyl ring, and thereafter with a compound of formula $(YR_p)_qZ_2$, wherein Y, R, z and q are defined as above and the substituents Z, same or different from each other, are halogen atoms or tosylate groups.

The preparation of the bridged ligands of the metallocene compounds of formula (I) wherein q is different from 0 and the group Cp is different from the group Cp', can be carried out by reacting a symmetric or asymmetric fulvene with an anionic salt of the substituted Cp group.

The metallocene compounds of formula (I) can be prepared by first reacting the bridged ligands prepared as described above, or the cyclopentadienylic compounds of formula (II) or (III), with a compound able to form a delocalized anion on the cyclopentadienyl rings, and thereafter with a compound of formula $MZ_4$, wherein M and the substituents Z are defined as above.

The metallocene compounds of formula (I) wherein q=0 and Cp is different from Cp' can be prepared by reacting the dianion of the ligand with a tetrahalide of the metal M, said reaction being carried out in a suitable solvent.

A particularly convenient method for preparing the metallocene compounds of formula (I), in which both Cp and Cp' groups are selected from the groups of formula (II) wherein m=4, is the hydrogenation reaction of the corresponding metallocene compounds in which both Cp and Cp' are selected from the groups of formula (III). The hydrogenation reaction is carried out in a solvent, such as $CH_2Cl_2$, in the presence of a hydrogenation catalyst, such as $PtO_2$, and hydrogen. The hydrogen pressures are preferably comprised between 1 and 100 bar, and the temperatures are preferably comprised between −50 and 50° C.

In the case at least one X substituent in the metallocene compound of formula (I) to be prepared is different from halogen, it is necessary to substitute at least one substituent Z in the obtained metallocene with at least one X substituent different from halogen.

The substitution reaction of substituents Z in the compound of formula (VI) with substituents X different from halogen is carried out by generally used methods. For example, when the substituents X are alkyl groups, the metallocenes can be reacted with alkylmagnesium halides (Grignard reagents) or with lithioalkyl compounds.

Non limitative examples of compounds of formula $(YR_p)_qZ_2$ are dimethyldichlorosilane, diphenyldichlorosilane, dimethyldichlorogermanium, 2,2-dichloropropane, 1,2-dibromoethane and the like.

Non limitative examples of compounds of formula $MZ_4$ are titanium tetrachloride, zirconium tetrachloride, hafnium tetrachloride.

According to an embodiment of the process according to the invention, the synthesis of the bridged ligands of the metallocene compounds of formula (I) wherein q is different from 0 and the group Cp is the same as the group Cp' is suitably performed by adding a solution of an organic lithium compound in an aprotic solvent to a solution of the compound (II) or (III) in an aprotic solvent. Thus, a solution containing the compound (II) or (III) in the anionic form is obtained and this is added to a solution of the compound of formula $(YR_p)_qZ_2$ in an aprotic solvent.

From the so obtained solution, the bridged ligand is separated by generally used methods. This is dissolved in an aprotic polar solvent, and to this solution a solution of an organic lithium compound in an aprotic solvent is added. The bridged ligand thus obtained is separated, dissolved in an aprotic polar solvent and thereafter added to a suspension of the compound $MZ_4$ in an apolar solvent. At the end of the reaction the solid product obtained is separated from the reaction mixture by generally used techniques.

During the whole process, the temperature is kept between −180° C. and 80° C. and preferably between −20° C. and 40° C.

Not limitative examples of apolar solvents which can be used in the above described process are pentane, hexane, benzene and the like.

Not limitative examples of aprotic polar solvents which can be used in the above described process are tetrahydrofurane, dimethoxyethane, diethylether, toluene, dichloromethane and the like.

In the catalyst of the invention, the aluminoxane used as component (B) can be obtained by the reaction between water and the organo-aluminium compound of formula $AlR^4_3$ or $Al_2R^4_6$, in which substituents $R^4$, same or different from each other are defined above, with the condition that at least one $R^4$ is not halogen. In this case, the molar ratios of Al/water in the reaction is comprised between 1:1 and 100:1.

The molar ratio between aluminium and the metal from the metallocene is comprised between 10:1 and about 5000:1, and preferably between about 100:1 and about 4000:1.

The alumoxane used in the catalyst according to the invention is believed to be a linear, branched or cyclic compound, containing at least one group of the type:

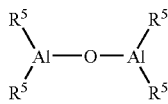

wherein substituents $R^5$, the same or different from each other, are $R^1$ or a group $—O—Al(R^5)_2$.

Examples of alumoxanes suitable for the use according to the present invention are methylalumoxane (MAO) and isobutylalumoxane (TIBAO).

Mixtures of differents alumoxanes are suitable as well.

Not limitative examples of aluminium compounds of formula $AlR_3$ or $Al_2R^4_6$ are:

$Al(Me)_3$, $Al(Et)_3$, $AlH(Et)_2$, $Al(iBu)_3$, $AlH(iBu)_2$, $Al(iHex)_3$, $Al(C_6H_5)_3$, $Al(CH_2C_6H_5)_3$, $Al(Ch_2CMe_3)_3$, $Al(CH_2SiMe_3)_3$, $Al(Me)_2iBu$, $Al(Me)_2Et$, $AlMe(Et)_2$, $AlMe(iBu)_2$, $Al(Me)_2iBu$, $Al(Me)_2Cl$, $Al(Et)_2Cl$, $AlEtCl_2$, $Al_2(Et)_3Cl_3$, wherein Me=methyl, Et=ethyl, iBu=isobutyl, iHex=isohexyl.

Among the above mentioned aluminium compounds, trimethylaluminium (TMA) and triisobutylaminium (TIBAL) are preferred.

Not limitative examples of compounds able to form a metallocene alkyl cation are compounds of formula $Y^+Z^-$, wherein $Y^+$ is a Bronsted acid, able to give a proton and to react irreversibly with a substituent $R^2$ of the compound of formula (I) and $Z^-$ is a compatible anion, which does not coordinate, which is able to stabilize the active catalytic species which originates from the reaction of the two compounds and which is sufficiently labile to be able to be removed from an olefinic substrate. Preferably, the anion $Z^-$ comprises one or more boron atoms. More preferably, the anion $Z^-$ is an anion of the formula $BAr^{(-)}_4$, wherein substituents Ar, the same or different from each other, are aryl radicals such as phenyl, pentafluorophenyl, bis(trifluoromethyl)phenyl. Particularly preferred is the tetrakis-pentafluorophenyl borate. Furthermore, compounds of formula $BAr_3$ can be suitably used.

The catalysts of the present invention can also be used on an inert support. That is by depositing the metallocene compound (A), or the reaction product of the metallocene (A) with component (B), or the component (B) and successively the metallocene compound (A), on the inert support such as for example, silica, alumina, styrene-divinylbenzene copolymers or polyethylene.

The solid compound so obtained, in combination with further addition of the alkyl aluminium compound as such or prereacted with water if necessary, is usefully employed in the gas phase polymerization.

The catalysts of the present invention can advantageously be used in a process for the homo- or copolymerization reaction of olefins.

According to a particular embodiment of the above process, the catalysts of the present invention can be profitably used in the homo-polymerization reaction of olefins, in particular of ethylene for the preparation of HDPE, or of α-olefins such as propylene and 1-butene.

When it is employed a bridged metallocene compound of formula (I) wherein q is different from 0 and the group Cp is the same as the group Cp', the obtained α-olefin homopolymers have an atactic structure and, therefore, are substantially amorphous.

In particular, with the catalyst of the present invention it is possible to prepare propylene oligomers which result to be endowed with allylic terminations; said oligomers can be suitably employed as comonomers in the copolymerization reactions of olefins.

Alternatively, when it is employed a metallocene compound of formula (I) wherein q=1 and the group Cp' is a non-substituted cyclopentadienyl group, the obtained α-olefin homopolymers have a predominantly syndiotactic structure.

Another interesting use of the catalysts according to the present invention is for the copolymerization of ethylene with higher olefins.

In particular, the catalysts of the invention can be used for the preparation of LLDPE. The LLDPE copolymers which are obtained have a content of ethylene units comprised between 80% and 99% by mols. Their density is comprised between 0.87 and 0.95 g/cc and they are characterized by a uniform distribution of the alpha-olefin comonomers.

The olefins useable as comonomers comprise alpha-olefins of the formula $CH_2=CHR$ wherein R is a straight, branched or cyclic alkyl radical containing from 1 to 20 carbon atoms, and cycloolefins.

Examples of these olefins are propylene, 1-butene, 1-pentene, 4-methyl-1-pentene, 1-hexene, 1-octene, 1-decene, 1-dodecene, 1-tetradecene, 1-esadecene, 1-octadecene, 1-eicosene, allylcyclohexane, cyclopentene, cyclohexene, norbornene, 4,6-dimethyl-1-heptene.

The copolymers may also contain small proportions of units deriving from polyenes, in particular from straight or cyclic, conjugated or non conjugated dienes such as, for example, 1,4-hexadiene, isoprene, 1,3-butadiene, 1,5-hexadiene, 1,6-heptadiene.

The units deriving from the alpha-olefins of the formula $CH_2=CHR$, from the cycloolefins and/or from the polienes are present in the copolymers in amounts of from 1% to 20% by mole.

The catalyst of the invention can also be used for the preparation of elastomeric copolymers of ethylene with alpha-olefins of the formula $CH_2=CHR$, wherein R is an alkyl radical having from 1 to 10 carbon atoms, optionally containing small proportions of units deriving from polyenes.

The saturated elastomeric copolymers contain from 15% to 85% by mole of ethylene units, the complement to 100 being constituted by units of one or more alpha-olefins and/or of a non conjugated diolefin able to cylopolymerize. The unsaturated elastomeric copolymers contain, together with the units deriving from the polymerization of ethylene and alpha-olefins, also small proportions of unsaturated units deriving from the copolymerization of one or more polyenes. The content of unsaturated units can very from 0.1 to 5% by weight, and it is preferably comprised between 0.2 and 2% by weight.

The elastomeric copolymers obtainable with the catalysts of the invention are endowed with valuable properties such as, for example, low content of ashes and uniformity of distribution of the comonomers within the copolymeric chain.

Moreover, a valuable property of said elastomeric copolymers is that their molecular weights are high enough to be of practical interest. In fact, the intrinsic viscosity values (I.V.) of said copolymers are generally higher than 2.0 dl/g and can reach values of 3.0 dl/g and higher. This is a considerable and unpredictable advantage over the copolymers obtainable with a metallocene compound according to the cited EP-A-604 908.

The useable alpha-olefins comprise, for example, propylene, 1-butene, 4-methyl-1-pentene. As non conjugated diolefins able to cyclopolymerize, 1,5-hexadiene, 1,6-heptadiene, 2-methyl-1,5-hexadiene can be used.

Polyenes useable comprise:

polyenes able to give unsaturated units, such as:

linear, non-conjugated dienes such as 1,4-hexadiene trans, 1,4-hexadiene cis, 6-methyl-1,5-heptadiene, 3,7-dimethyl-1,6-octadiene, 11-methyl-1,10-dodecadiene;

monocyclic diolefins such as, for example, cis-1,5-cyclooctadiene and 5-methyl-1,5-cyclooctadiene;

bicyclic diolefins such as for example 4,5,8,9-tetrahydroindene and 6 and/or 7-methyl-4,5,8,9-tetrahydroindene;

alkenyl or alkyliden norbornenes such as for example, 5-ethyliden-2-norbornene, 5-isopropyliden-2-norbornene, exo-5-isopropenyl-2-norbornene;

polycyclic diolefins such as, for example, dicyclopentadiene, tricyclo-[6.2.1.0$^{2,7}$]4,9-undecadiene and the 4-methyl derivative thereof;

non-conjugated diolefins able to cyclopolymerize, such as 1.5-hexadiene, 1,6-heptadiene, 2-methyl-1,5-hexadiene; conjugated dienes, such as butadiene and isoprene.

A further interesting use of the catalysts according to the present invention is for the preparation of cycloolefin polymers. Monocyclic and polycyclic olefin monomers can be either homopolymerized or copolymerized, also with linear olefin monomers. Non limitative examples of cycloolefin polymers which can be prepared with the catalyst of the present invention are described in the European patent applications No. 501,370 and No. 407,870, the contents of which are understood to be incorporated in the present description as a result of their mention.

Polymerization processes which use the catalysts of the invention can be carried out in liquid phase, in the presence or not of an inert hydrocarbon solvent, or in gaseous phase. The hydrocarbon solvent can be either aromatic such as, for example, toluene, or aliphatic such as, for example, propane, hexane, heptane, isobutane, cyclohexane.

The polymerization temperature generally ranges from about 0° C. to about 250° C. In particular, in the processes for the preparation of HDPE and LLDPE, it is generally comprised between 20° C. and 150° C. and, particularly, between 40° C. and 90° C., whereas for the preparation of the elastomeric copolymers it is generally comprised between 0° C. and 200° C. and, particularly, between 20° C. and 100° C.

The molecular weight of polymers can be varied by simply varying the polymerization temperature, the type or the concentration of the catalyst components or, and this represent an advantage of the invention, by using molecular weight regulators such as, for example, hydrogen.

The fact that the catalysts of the invention are sensitive to hydrogen as a molecular weight regulator is unexpected in view of the fact that, if the polymerization is carried out in the presence of a metallocene compound according to the cited EP-A-604 908, the hydrogen has no effect on the molecular weight of the obtained polymers, even if used in relevant amounts.

The molecular weight distribution can be varied by using mixtures of different cyclopentadienyl compounds, or by carrying out the polymerization in many steps which differ for the polymerization temperatures and/or for the concentrations of the molecular weight regulator.

The polymerization yield depends on the purity of the metallocene components in the catalyst. Therefore the metallocene obtained by the process of the invention may be used as such, or subjected to purification treatments.

Particularly interesting results are obtained when the components of the catalyst are contacted among them before the polymerization. The contact time is generally comprised between 1 and 60 minutes, preferably between 5 and 20 minutes. The pre-contact concentrations for the metallocene component (A) are comprised between $10^{-2}$ and $10^{-8}$ mol/l, whereas for the component (B) they are comprised between 10 and $10^{-3}$ mol/l. The precontact is generally carried out in the presence of a hydrocarbon solvent and, optionally, of small amounts of monomer.

The following examples are supplied for purely illustrative and not limiting purpose.

Characterisations

The intrinsic viscosity [η] has been measured in tetrahydronaphtalene at 135° C.

The molecular weight distribution has been determined by GPC using a WATERS 150 instrument in orthodiclorobenzene at 135° C.

The Melt Index (MI) has been measured under the following conditions:

Condition E ($I_2$: ASTM D-1238) at 190° C. with a 2.16 kg load;

Condition F ($I_{21}$: ASTM D-1238) with a 21.6 kg load;

the Melt Flow Ratio (MFR) is equal to $I_{21}/I_2$.

The percentage by weight of comonomers in the copolymer has been determined according to Infra-Red (IR) techniques.

The real density has been measured according to the ASTM D-1505 method by deeping of an extruded polymer sample in a density gradient column.

The Differential Scanning Calorimetry (DSC) measurements have been carried out on a DSC-7 apparatus of Perkin Elmer Co. Ltd., according to the following procedure. About 10 mg of sample are heated to 180° C. with a scanning speed equal to 10° C./minute; the sample is kept at 180° C. for 5 minutes and thereafter is cooled with a scanning speed equal to 10° C./minute. A second scanning is then carried out according to the same modalities as the first one. Values reported are those obtained in the second scanning.

The solubility in xylene at 25° C. has been determined according to the following modalities. About 2.5 g of polymer and 250 ml of xylene are placed in a round-bottomed flask provided with cooler and reflux condenser, kept under nitrogen. This is heated to 135° C. and is kept stirred for about 60 minutes. This is allowed to cool under stirring to 25° C. The whole is filtered off and after evaporation of the solvent from the filtrate until a constant weight is reached, the weight of the soluble portion is calculated.

Preparation of the Ligands

EXAMPLE 1

Synthesis of 2,3-cyclotetramethyleneindene

A mixture of 50 g of benzoic acid (409 mmol) and 35.2 g of cyclohexene (428 mmol) was added to 200 g of polyphosphoric acid (Aldrich). After stirring at 80–90° C. for 3 hours, 300 ml of a saturated solution of ammonium sulphate was added to the reddish brown reaction mixture. The resulting mixture was then extracted three times with 200 ml of dichloromethane. Organic portions were combined and washed succesively with 300 ml of a 5% acqueous solution of ammonium hydroxide and 300 ml of saturated sodium carbonate. The organic layer then was dried over Na$_2$SO$_4$, concentrated and vaccuum distilled (boiling point 110° C. at 0.1 mmHg) to yield 31.2 g of 2,3-cyclotetramethyleneindan-1-one.

4.0 g of sodium borohydride (107 mmol) was added in portions to a mixture of 20.0 g (107 mmol) of 2,3-cyclotetramethyleneindan-1-one and 40 g (107 mmoli) of CeCl$_3$.7H$_2$O in 250 ml of methanol. A vigorous gas evolutiom occurred. After stirring at 40° C. for 3 hours, the reaction crude was neutralised with 10% aqueous HCl. The mixture was then extracted 3 times with 250 ml of ether, dried over Na$_2$SO$_4$, and concentrate to yield 16.0 g of white solid.

The solid product was mixed with 0.16 g of p-toluenesulphonic acid monohydrate in 100 ml toluene and was refluxed at 110° C. After 2 hours the reaction crude was washed successively with 250 ml of a saturated aqueous solution of sodium bicarbonate and 250 ml of water. The organic then was dried over Na$_2$SO$_4$, concentrated, and vaccuun distilled (b.p. 100° C. at 0.15 mm Hg) to yield 12.86 g of a light yellow liquid, identified as pure 2,3-cyclotetramethyleneindene by its $^1$H NMR spectra. A small amount of 1,2-cyclotetramethyleneindene was also detected in the product.

EXAMPLE 2

Synthesis of 1,2-cyclotrimethyleneindene

A mixture of 116.8 g of benzoic anhydride (513 mmol) and 69.8 g of cyclopentene (513 mmol) was added to 1000 g of polyphosphoric acid (Aldrich). After stirring at 70–80° for 3 hours, a saturated solution of ammonium sulfate (500 ml) was added to the reddish-brown reaction mixture. The resulting mixture was then extracted with dichloromethane (3×300 mL). organic portions were combined and washed successively with aqueous ammonium hydroxide (5% solution, 500 mL) and saturated sodium carbonate (500 mL). The organic solution was then dried over Na$_2$SO$_4$, concentrated, and vacuum distilled (b.p. 125° C. at 6 mmHg) to yield 42 g of 2,3-cyclotrimethyleneindan-1-one.

1.06 g of sodium borohydride (28.3 mmol) was added in portions to a mixture of 4.87 g (28.3 mmol) of 2,3-cyclotrimethyleneindan-1-one and 10.6 g (28.3 mmoli) of CeCl$_3$.7H$_2$O in 250 ml of methanol. A vigorous gas evolutiom occurred. After stirring at 40° C. for 3 hours, the reaction crude was neutralised with 10% aqueous HCl. The mixture was then extracted 3 times with 250 ml of ether, dried over Na$_2$SO$_4$, and concentrate to yield 4.2 g of white solid.

A mixture of the off-white solid above (4.2 g) and p-toluenesulfonic acid monohydrate (0.84 g) in benzene (100 mL) was refluxed at 80° C. After 2 hours, the reaction mixture was washed successively with saturated sodium bicarbonate (100 mL) and water (100 mL). The organic layer was then dried over Na$_2$SO$_4$, concentrated, and vacuum distilled (b.p. 100° C. at 5 mmHg) to yield 2,3 g of a light yellow liquid, identified as 1,2-cyclotrimethyleneindene by its $^1$H-NMR spectrum.

EXAMPLE 3

Synthesis of 1,2-cyclohexamethyleneindene

A mixture of benzoic anhydride (85.0 g, 376 mmol) and cyclooctene (82.7 g, 751 mmol) was added to polyphosphoric acid (Aldrich, 200 g). After stirring at 80–90° C. for 3 hours, a saturated solution of ammonium sulfate (300 ml) was added to the reddish-brown reaction mixture. The resulting mixture was then extracted with dichloromethane (3×200 ml). Organic portions were combined and washed successively with aqueous ammonium hydroxide (5% solution, 300 ml) and saturated sodium carbonate (300 ml). The organic solution was then dried over Na$_2$SO$_4$, concentrated, and vacuum-distilled (b.p. 125–130° C. at 0.3 mmHg) to yield 60.5 g of 2,3-cyclohexamethyleneindan-1-one.

4.4 g of sodium borohydride (119 mmol) was added in portions to a mixture of 25.4 g (119 mmol) of 2,3-cyclohexamethyleneindan-1-one and 43.9 g of CeCl$_3$.7H$_2$O (119 mmol) in 250 ml of methanol. A vigorous gas evolution occurred. After stirring at 40° C. for 3 hours, the reaction crude was neutralized with 10% aqueous HCl, then extracted with Et2O (3×250 ml), dried over Na$_2$SO$_4$, and concentrated to yield 23.1 g of a white solid.

A mixture of the white solid above (23.1 g) and p-toluenesulfonic acid monohydrate (1 g) in benzene (100 ml) was refluxed at 80° C. After 2 hours, the reaction mixture was washed successively with saturated sodium bicarbonate (250 ml) and water (250 ml). The organic layer was then dried over Na$_2$SO$_4$, concentrated, and vacuum-distilled (b.p. 115° C. at 0.2 mm Hg) to yield 14.6 g of a light yellow liquid, identified as pure 1,2-cyclohexamethyleneindene by its $^1$H-NMR.

EXAMPLE 4

Synthesis of Octahydrofluorene

In a 250 ml three neck round bottom flask, equipped with a mechanical stirrer, a thermometer and a reflux condenser 16.276 g of polyphosphoric acid was charged and heated to a temperature of 70° C. 16.276 g of 1-cyclohexenecarboxylic acid and 10.592 g of cyclohexane were added dropwise maintaining a temperature of the reaction mass below 100° C. The mixture was stirred at 78° C. for additional 4.5 hours. The dark brown reaction mass was was poured onto 237 g of ice and neutralised with 89 g aqueous ammonium sulphate solution in 474 g of water. The resulting mixture was then extracted 4 times with 300 ml of petroleum ether and 300 ml of diethyl ether. All organic layers were combined, washed successively with 5% aqueous ammonium hydroxide, brine dried over magnesium sulphate and concentrated in vacuum. Fractional distillation (b.p. 130° C. at 3.0 mmHg) of this crude product yielded 10.294 g of 1,2,3,4,4a,5,6,7,8,9a-decahydro-9H-fluoren-9-one. $^1$H-NMR (CDCl$_3$): δ 2.73 (q, J=7 Hz, 1 H), 2.2–0.5 (m, 17 H).

A mixture of the above product (4.08 g, 21.47 mmol) and p-toluene-sulfonhydrazide (4.798 g, 25.76 mmol) in absolute ethanol (5 ml) was refluxed for 24.5 hours. The reaction mixture was allowed to cool to room temperature, the solid filtered, washed with absolute ethanol (4×5 ml) and air dried to yield 4.06 g (53%) of 1,2,3,4,4a,5,6,7,8,9a-decahydrofluoren-9-p-toluenesulfonhydrazone, m.p. 160–162° C. $^1$H-NMR (CDCl$_3$): δ 8.21 (broad d, J=8 Hz, 2 H), 7.35 (broad s, 1 H), 7.30 (broad d, J=8 Hz, 2 H), 2.55 (dd, J=10 Hz, 2.8 Hz, 1 H), 2.42 (3 H), 2.07–2.04 (m, 4 H), 1.9–1.55 (m, 8 H), 1.30–1.10 (m, 5 H).

To a solution of this product (276.5 mg, 0.77 mmol) in Et2O (15 ml) was added 1.65 ml (2.35 mmol) of methyllithium 1.4 M in Et2O under nitrogen at –0° C. The resulting orange reaction mixture was kept at 0° C. for 2 hours and then stirred at ambient temperature for 15.5 hours. A mixture of pentane (15 ml) and water (5 ml) was added. The acqueous layer was extracted with pentane (4×20 ml). All organic layers were combined and concentrated to yield 109.0 mg of octahydrofluorene. $^1$H-NMR (CDCl$_3$): δ 5.6 (d, J=2.21 Hz, 1 H), 2.62–0.8 (m, 17 H).

EXAMPLE 5

Synthesis of 9-methyl-octahydrofluorene

To a solution of 1,2,3,4,4a,5,6,7,8,9a-decahydrofluoren-9-one (90.7 mg, 0.477 mmol) in tetrahydrofuran (5 ml), 0.35 ml (1.05 mmol) of methylmagnesium bromide (3.0 M in Et2O) was added dropwise under nitrogen at –78° C. The resulting cloudy mixture was kept at –78° C. for 3 hours and then allowed to warm to room temperature and stirred for 14 hours. The reaction mixture was acidified with 15% aqueous HCl (5 ml), followed by extraction in Et2O (4×20 ml). All organic layers were combined, washed with water, brine, dried over anhydrous magnesium sulfate, and concentrated in vacuo to give 82.5 mg (92%) of 2,3,4,4a,5,6,7,8-octahydro-9-methyl-1H-fluorene and 1,3,4,5,6,7,8,9a-octahydro-9-methyl-2H-fluorene in the ratio of 3 to 1. $^1$H-NMR (CDCl$_3$): δ 2.6–0.9 (m), 13C NMR: 155.77, 136.49, 133.51, 111.70, 61.12, 50.29, 42.14, 29.74, 27.41, 25.46, 25.11, 23.38, 22.81.

EXAMPLE 6

Synthesis of Tricyclo [6.3.0.0$^{3,7}$] Undeca-1,3(7)-diene

A stirred suspension of 1-cyclopentene carboxylic acid (11.2 g, 100 mmol) and cyclopentene (13.6 g, 200 mmol) was added slowly to stirring polyphosphoric acid (Aldrich, 300 g) at 60° C. in a 250 mL flask. The reaction mixture was stirred at 70–80° C. for 4 hours under nitrogen. The dark brown reaction mixture was cooled to 30° C. and poured on 300 g of ice and vigorously stirred in a cooling bath. The brown mass was then neutralized with a saturated solution of ammonium sulfate (200 ml). The resulting mixture was then extracted with Et2O (5×200 mL). The combined organic layers were washed successively with water, saturated sodium bicarbonate solution and water. The washed organic extract was then dried over anhydrous MgSO4 and concentrated in vacuo. The residue was distilled at 130–135° C. at 4 mmHg to yield 3.5 g, 25%, about 90% purity. This product was chromatographed on silica gel using hexane and ethyl acetate as eluent to obtain pure cis-tricyclo [6.3.0.0$^{3,7}$] undec-1(8)-en-2-one. $^1$H-NMR (CDCl$_3$): δ 3.2 (m, 1 H), 3.1 (m, 1 H), 2.5 (m, 2 H), 2.4 (m, 4 H), 1.9 (m, 1 H), 1.6 (m, 4 H), 1.3 (m, 1 H).

The above enone (1.6 g, 10 mmol) was dissolved in methanol (25 mL) and p-toluenesulfonhydrazide (2.4 g, 12.5 mmol) was added to the solution. The solution was refluxed for 4 hours under nitrogen. The solution was then concentrated in vacuo and the residue dissolved in methylene chloride (25 mL)and to the solution was added hexane (12 mL). The turbid solution was cooled to obtain off-white crystalline hydrazone (2.3 g). $^1$H-NMR (CDCl$_3$): δ 7.8–7.2 (m, 4 H), 3.7–3.0 (m, 1 H), 3.3–2.8 (ddd, 1 H), 2.3 (3 H), 2.2–1.2 (m, 12 H).

To a solution of the above hydrazone (0.7 g, 2 mmol) in dry THF (10 mL) was added 5 mL of 1.4 M methyl lithium solution in Et$_2$O (7 mmol) slowly at –78° C. under nitrogen. The reaction mixture was stirred for 1 hour, then allowed to slowly warm to room temperature and finally stirred for additional 3 hours. The reaction mixture was quenched with saturated ammonium chloride solution (5 mL) and extracted with Et$_2$O (20×3 mL). The organic extracts were combined and dried over anhydrous MgSO$_4$, concentrated in vacuo and the residue chromatographed on neutral alumina using hexane as eluent to obtain tricyclo[6.3.0.0$^{3,7}$] undeca-1,3 (7)-diene (130 mg). $^1$H-NMR (CDCl$_3$): δ 5.8 (d, 1 H), 3.5–3.1 (m, 1 H), 2.9–1.3 (m, 12 H).

EXAMPLE 7

Synthesis of Dimethylbis(2,3-cyclotetramethyl-eneinden-1-yl)-silane 18.8 ml (2.5M in hexane) of n-butyl lithium was added dropwise to a mixture of 8.0 g (47 mmol) of 2,3-cyclotetramethyleneindene obtained from Example 1 in 100 mL of anhydrous ether at 0° C. The reaction mixture was allowed to stir at room temperature for 3 hours. It was then cooled to 0° C. and 3.0 g (23.5 mmoli) of dichlorodimethylsilane was added. After stirring at room temperature for 17 hours, the reaction crude was filtered, concentrated and distilled. The product was crystallised twice in ethanol to yield 3.4 g of product having a melting point of 110–112° C. $^1$H-NMR (CDCl$_3$): δ 7.60–7.02 (m, 8 H), 3.62 and 3.55 (2 broad s, 2 H total), 2.80–1.40 (m, 16 H), –0.20, –0.30 and –0.32 (3 s, 6 H total).

EXAMPLE 8

Synthesis of 1,2-bis(1,2-cyclotetramethyleneindenyl)ethane 21.2 ml (2.5M in hexane) of n-butyl lithium was added dropwise to a mixture of 9.0 g (53 mmol) of 2,3-cyclotetramethyleneindene obtained from Example 1 in 100 mL of anhydrous ether at 0° C. The reaction mixture was allowed to stir at room temperature for 3 hours. It was then cooled to –78° C. and 4.68 g (26.5 mmol) of dibromoethane was added. The mixture was warmed to room temperature and stirred for 30 hours. The reaction crude was washed with ammonium chloride, concentrated and distilled to remove any unreacted starting material. The product was then crystallised in ethanol to yield 3.2 g of product having a melting point of 170–173° C. $^1$H-NMR (CDCl$_3$): δ 7.3–7.0 (m, 8 H), 3.15 (broad s, 2 H), 2.75–1.2 (m, 20 H).

EXAMPLE 9

Synthesis of 2-cyclopentadienyl-2-(1,2-cyclotetramethyleneindenyl)propane n-Buthyllithium (2.5 M solution in hexane, 7.5 mmol) was added dropwise to a stirring solution of 2,3-cyclotetramethyleneindene (0.85 g, 5 mmol) in 40 mL THF at 0° C. The solution was warmed to room temperature and stirred for an additional 16 hours. Solvents were evaporated and the solids remaining were washed with hexane. The solids were then resuspended in THF and 6,6-dimethylfulvene (Aldrich) was added dropwise at 0° C. to the stirred solution. After the addition was complete, the reaction was allowed to warm to room temperature and stirred an additional 12 hours. The reaction was quenched with a saturated solution of ammonium sulfate, the organic layer was collected and dried over MgSO$_4$, then concentrated in vacuo. The oily product was further purified by distillation to remove the starting materials, and a final purification was done by treating the above oil with two equivalents of methyllithium in ether (1.4 M, 10 mmol), collecting the solids and washing away impurities with anhydrous Et2O. A pale yellow powder (1.33 g) was collected and identified by NMR as the dilithium salt of 2-cyclopentadienyl-2-(1,2-cyclotetramethyleneindenyl)propane.

Preparation of the Metallocenes

EXAMPLE 10

Synthesis of Dimethylsilanediyl-bis(2,3-cyclotetramethyleneindene-1-yl)zirconium dichloride 2.2 g (5.5 mmol) of dimethylbis(2,3-cyclotetramethyleneinden-1-yl)silane was dissolved in 100 ml $Et_2O$. The temperature was decreased to 0° C. and 8 ml of a 1.4 molar solution of methyllithium in $Et_2O$ was added dropwise to the stirred solution. After the addition was complete, the solution was warmed to room temperature and stirred for 17 hours. This solution was then cannulated into a stirred flask containing 1.3 g (5.5 mmol) of $ZrCl_4$ suspended in dry pentane at 0° C. The reaction mixture was then allowed to warm to room temperature and stirred for 8 hours before being filtered. The solids collected on the filter were washed with $Et_2O$ and pentane prior to being dried in vacuo. 2.58 g of a bright orange powder were obtained, which were further purified by extraction with dichloromethane. The solid, orange product obtained by solvent removal consists of a mixture of racemic and meso (about 1:1) dimethylsilanediyl-bis(2,3-cyclotetramethyleneinden-1-yl)zirconium dichloride, as shown by its $^1$H-NMR spectrum ($CDCl_3$): δ 7.7–6.7 (m, 8 H), 3.2–1.3 (m, 16 H), 1.4, 1.23, 1.1 (3 singlets in about 1:2:1 ratio, 6 H total).

EXAMPLE 11

Synthesis of Dimethylsilanediyl-bis(octahydrofluorenyl)zirconium Dichloride 1,749 g of dimethylsilanediyl-bis(2,3-cyclotetramethyleneinden-1-yl)zirconium dichloride obtained in Example 10, 105 mg of $Pt_2O$ and 100 ml of freshly distilled, anhydrous $CH_2Cl_2$ were charged in a 250 ml autoclave equipped with a magnetic stirbar and under nitrogen. The nitrogen atmosphere was replaced with 5 bar hydrogen and the mixture was stirred at room temperature for 4 hours. After releasing the pressure, the suspension was filtered under nitrogen, the residue washed with $CH_2Cl_2$ until the whashings were colourless, the latter reunited to the filtrate, and all volatiles removed in vacuo to leave 1,354 g of a yellow-green solid which was further purified by crystallization from toluene at −20° C., to yield 1,0 g of pure, crystalline dimethylsilanediyl-bis(octahydrofluorenyl)zirconium dichloride as shown by its $^1$H NMR ($CDCl_3$): δ 2.95–2.7 (m, 4 H), 2.65–2.2 (m, 12 H total), 2.05–1.3 (m, 16 H), 0.85 (s, 6 H).

EXAMPLE 12

Synthesis of Isopropyliden(cyclopentadienyl) (2,3-cyclotetramethyleneinden-1-yl)zirconium Dichloride To a flask containing 1.33 g of the dilithium salt of 2-cyclopentadienyl-2-(1,2-cyclotetramethyleneindenyl)propane prepared as described in Example 9, 1.16 g (5 mmol) of ZrCl4 were added. The powders were suspended in fresh pentane and stirred overnight. Solids were collected by filtration and washed with pentane, then dried in vacuo. A light brown powder (1.82 g) was recovered, which was shown to be the title product by $^1$H-NMR analysis.

EXAMPLE 13

Synthesis of Isopropyliden(cyclopentadienyl)(2,3-cyclotetramethyleneinden-1-yl)hafnium Dichloride To a flask containing 1.67 g of the dilithium salt of 2-cyclopentadienyl-2-(1,2-cyclotetramethyleneindenyl)propane prepared as described in Example 9, 1.6 g (5 mmol) of $HfCl_4$ were added. The powders were suspended in fresh pentane and stirred overnight. Solids were collected by filtration and washed with pentane, then dried in vacuo. A yellow powder (2.22 g) was recovered, which was shown to be the title product by $^1$H-NMR analysis.

Polimerizations

Methylaluminoxane (MAO) A commercial product (Schering, MW 1400) was used in solution of 30% by weight in toluene. After having removed the volatile fractions under vacuum the glassy material was finely crushed in order to obtain a white powder that is further treated under vacuum (0,1 mm Hg) for 4 hours at a temperature of 40° C.; The so obtained powder shows good flowing properties;

Isobutylaluminoxane (TIBAO)

The commercial product (Schering) was used as such in a solution of 30% by weight in cyclohexane.

Modified Methylalumoxane (M-MAO)

The commmercial (Ethyl) isopar C solution (62 g Al/L) was used as received.

Preparation of the Catalyst Solution

The catalyst solution was prepared by dissolving a known amount of the metallocene in a known amount of toluene, then transferring an aliquot of this solution into a toluene solution containing the desired amount of the cocatalyst, obtaining a clear solution which was stirred for 5–10 min. at ambient temperature and then injected into the autoclave at the polymerization temperature in the presence of the monomer.

EXAMPLE 14

Polymerization of Ethylene

In a Büchi autoclave with a glass body of 1 l, equipped with a jacket, helic stirrer and thermoresistance, and connected to a thermostat to control the temperature, degassed with a solution of $AliBu_3$ in hexane and heat dryed under a nitrogen stream, 0.4 l of n-hexane (purified by passing through an alumina column) was added in a nitrogen stream and the temperature was brought to 50° C.

A toluene solution containing 0.1 mg of dimethylsilanediylbis (2,3-cyclotetramethyleneinden-1-yl) zirconium dichloride prepared as described in example 10 and 0.9 mmol as Al of TIBAO was injected in the autoclave at 50° C. under ethylene flow, the pressure raised to 4 bar, and the polymerization carried out at constant pressure and temperature for 1 hour. 8.5 g of polyethylene were isolated having an intrinsic viscosity of 13.4 dL/g.

EXAMPLE 15

Polymerization of Ethylene

In a 1.35-L Jacketed stainless-steel autoclave, equipped with an anchor stirrer and a thermoresistance, connected to a thermostat for temperature control, previously dried at 70° C. under a monomer stream, 45 mg H2O and 0.7 L of hexane (purified by passing through an activated alumina column) were charged under a flow of ethylene. The autoclave was then thermostated at 80° C.

5.7 mL of a toluene solution containing 0.56 mg of dimethylsilanediylbis(2,3-cyclotetramethyleneinden-1-yl) zirconium dichloride prepared as described in example 10 and 5 mmol as Al of AliBu3 was injected in the autoclave through a stainless-steel vial, the pressure raised to 11 bar, and the polymerization carried out at constant pressure and temperature for 1 hour. 17.2 g of polyethylene were isolated having an intrinsic viscosity of 8.2 dL/g.

EXAMPLE 16

Polymerization of Ethylene

The polymerization was carried out as in example 15, but using 90 mg of $H_2O$ and a catalyst prepared dissolving 1.13 mg of dimethylsilanediylbis(octahydrofluorenyl)zirconium dichloride as prepared in example 11 and 10 mmol as Al of AliBu3 in 11 mL of toluene. 15 g of polyethylene were isolated having an intrinsic viscosity of 2.4 dL/g.

EXAMPLE 17

Polymerization of Propylene 750 g of propylene were charged in a 2.3-L jacketed stainless-steel autoclave, equipped with stirrer and thermoresistance, connected to a thermostat for temperature control, previously dried at 70° C. in a stream of propylene. The autoclave was then thermostatted at 50° C. 25.8 mL of a toluene solution containing 5 mg of dimethylsilanediylbis-(2,3-cyclotetramethyleneinden-1-yl)zirconium dichloride prepared as described in example 10 and 1.04 g of MAO were injected in the autoclave through a stainless-steel vial, and the polymerization carried out at constant temperature for 1 hour. 103 g of atactic polypropylene were isolated having an intrinsic viscosity of 0.26 dL/g.

EXAMPLE 18

Oligomerization of Propylene 750 g of propylene were charged in a 2.3-L jacketed stainless-steel autoclave, equipped with stirrer and thermoresistance, connected to a thermostat for temperature control, previously dried at 70° C. in a stream of propylene. The autoclave was then thermostatted at 50° C. 25.8 mL of a toluene solution containing 4.6 mg of dimethylsilanediyl-bis-(octahydrofluorenyl)zirconium dichloride prepared as described in example 11 and 1.04 g of MAO were injected in the autoclave through a stainless-steel vial, and the polymerization carried out at constant temperature for 1 hour. 4 g of propylene oligomers were isolated which had an average oligomerization degree of 45. $^1$H-NMR analysis showed the oligomers to be about 95% allyl-terminated.

EXAMPLE 19

Polymerization of Propylene 480 g of propylene were charged in a 1.35-L jacketed stainless-steel autoclave, equipped with stirrer and thermoresistance, connected to a thermostat for temperature control, previously dried at 70° C. in a stream of propylene. The autoclave was then thermostatted at 50° C. 14 mL of a solution containing 7 mg of isopropyliden(cyclopentadienyl)(2,3-cyclotetramethyleneinden-1-yl)zirconium dichloride prepared as described in example 12 and dissolved in 7 mL toluene and 7 mL of M-MAO solution in isopar C were injected in the autoclave through a stainless-steel vial, and the polymerization carried out at constant temperature for 1 hour. 201 g of polypropylene were isolated which had intrinsic viscosity of 0.61 dL/g, melting point 108.8° C. with a $\Delta H$ of 26.4 J/g, and $M_w/M_n$=2.29. $^{13}$C-NMR analysis showed that the polymer is prevailingly syndiotactic.

EXAMPLES 20–23

Copolymerization of Ethylene with 1-butene

In a 2.62 l steel autoclave equipped with blade stirrer, 3.8 mmol of water, 1.26 l of liquid propane, and the quantities of ethylene, 1-butene and hydrogen indicated in Table 1 were introduced under anhydrous nitrogen atmosphere. The temperature was raised to 45° C., and 5 ml of a toluene solution of 7.7 mmol of triisobutyl aluminium (TIBAL) and the quantity of dimethylsilanylbis(2,3-cyclotetramethyleneinden-1-yl)zirconium dichloride indicated in Table 1, precontacted for 5 minutes in the absence of monomers, was introduced. Thereafter, the temperature was raised to 50° C. and the pressure of ethylene and hydrogen was kept constant for the whole test, carried out under stirring during 2 hours. After removal of the unreacted monomers, the polymer was separated by washing with methanol and drying under vacuum.

The polymerization conditions and yields are reported in Table 1. The characterization data of the copolymers obtained are reported in Table 2.

EXAMPLES 24–27 (COMPARISON)

Copolymerization of Ethylene with 1-butene

It was worked according to the procedure described in Examples 20–23, but with the difference that dimethylsilanyl-bis(fluorenyl)zirconium dichloride was used instead of dimethylsilanylbis(2,3-cyclotetramethyleneinden-1-yl)zirconium dichloride, and that the polymerization was carried out at a temperature of 40° C.

The polymerization conditions and yields are reported in Table 1. The characterization data of the copolymers obtained are reported in Table 2.

By comparing these data with those of the copolymers obtained in Examples 20–23 it clearly appears that, while in these polymerizations the hydrogen has no effect on the molecular weight of the obtained polymers, the use of hydrogen in polymerization reactions carried out with the catalysts according to the invention,even if it is used in low amounts so that the yields of the process are not negatively affected, makes it possible to regulate the molecular weight of the obtained polymers up to Melt Index values of practical interest.

EXAMPLES 28–30

Copolymerization of Ethylene with Propylene

In a 4,25 liter autoclave equipped with a stirrer, manometer, temperature indicator, system for loading the catalyst, monomer feed lines and a thermostating jacket, purged with ethylene at 80° C., the amount of propylene and ethylene reported in Table 3 were loaded at room temperature. The autoclave was then brought to a temperature of 5° C. lower than the polymerization temperature.

The catalyst solution was prepared as follows. A solution of TIBAO in toluene (0.2 gr TIBAO/ml solution) was added to a solution of dimethylsilanylbis(2,3-cyclotetramethyl-eneinden-1-yl)zirconium dichloride in toluene (3 ml toluene/mg metallocene). This was maintained under stirring at a temperature of 20° C. for 5 minutes, then the solution was injected into the autoclave under a pressure of an ethylene/propylene mixture in a ratio such to maintain in solution the relative concentrations as reported above. The temperature was then rapidly brought to values required for polymerization. The polymer obtained was isolated by removing non-reacted monomers, and then dried under vacuum.

The polymerization conditions, the yields and the characterization data of the copolymers obtained are reported in Table 3. No melting point is detectable at the DSC analysis.

By comparing these data with those of the copolymers of Examples 1–5 of EP-A-632 066, obtained with a catalyst based on dimethylsilanylbis(fluorenyl)zirconium dichloride, it clearly appears that at a parity of comonomer content the intrinsic viscosities of the polymers of EP-A-632 066 are considerably lower than those of the polymers obtained with the catalyst of the invention.

TABLE 1

| EXAMPLE | zirconocene (mg) | Al/Zr (mol) | 1-butene (ml) | ethylene (bar) | $H_2$ (bar) | yield (g pol.) | activity ($Kg_{pol}/g_{Zr}h$) |
|---|---|---|---|---|---|---|---|
| 20 | 4.30 | 1000 | 220 | 17.3 | 0 | 172 | 122.1 |
| 21 | 4.00 | 1075 | 220 | 17.3 | 0.05 | 152 | 116.0 |
| 22 | 4.00 | 1075 | 140 | 18.9 | 0.06 | 205 | 156.4 |
| 23 | 4.00 | 1075 | 300 | 16.4 | 0.07 | 206 | 157.2 |
| 24 (COMP.) | 6.00 | 1000 | 200 | 16.2 | 0.03 | 160 | 80.2 |
| 24 (COMP.) | 6.00 | 1000 | 160 | 16.7 | 0.13 | 265 | 132.8 |
| 25 (COMP.) | 6.00 | 1000 | 170 | 17.3 | 0.74 | 125 | 62.6 |
| 26 (COMP.) | 6.00 | 1000 | 190 | 18.3 | 2.06 | 15 | 7.5 |

TABLE 2

| | | Melt Index | | | | | DSC | | | xylene |
|---|---|---|---|---|---|---|---|---|---|---|
| EXAMPLE | [η] (dl/g) | $I_2$ (g/10') | $I_{21}$ (g/10') | MFR | 1-butene (w %) | density (g/ml) | Tm (II) (° C.) | $\Delta H_f$ (J/g) | $M_w/M_n$ | soluble (w %) |
| 20 | 1.91 | n.d. | 7.5 | n.d. | 10.7 | 0.9051 | 93 | 57 | n.a. | n.a. |
| 21 | 1.78 | 0.57 | 16.5 | 28.9 | 11.1 | 0.9030 | 95 | 73 | 3.6 | 3.6 |
| 22 | 1.65 | 1.10 | 31.0 | 28.2 | 9.1 | 0.9165 | 106 | 88 | 3.6 | n.a. |
| 23 | 1.48 | 2.82 | 68.1 | 24.1 | 17.1 | 0.9026 | 88 | 57 | n.a. | 15.7 |
| 24 (COMP.) | 3.66 | n.d. | n.d. | n.d. | 13.0 | 0.8940 | 78 | 23 | n.a. | n.a. |
| 25 (COMP.) | 4.45 | n.d. | n.d. | n.d. | 9.7 | 0.9000 | 92 | 73 | 2.9 | n.a. |
| 26 (COMP.) | 3.82 | n.d. | n.d. | n.d. | 13.0 | 0.9032 | 92 | 77 | n.a. | 0.2 |
| 27 (COMP.) | 3.09 | n.d. | n.d. | n.d. | n.a. | n.a. | n.a. | n.a. | n.a. | n.a. | n.d. = not determinable
n.a. = not available

TABLE 3

| EXAMPLE | Zr (mmol · $10^{-3}$) | Al/Zr (mol) | $C_2$ liq. phase (wt %) | P tot. (bar) | T (° C.) | time (min) | yield (g) | activity ($Kg_{pol}/g_{Zr}$) | $C_2$ units (wt %) | I.V. (dl/g) |
|---|---|---|---|---|---|---|---|---|---|---|
| 28 | 4.31 | 2610 | 20.00 | 29.3 | 40 | 120 | 48 | 849.4 | 48.0 | 2.04 |
| 29 | 4.31 | 2610 | 29.00 | 35.3 | 40 | 120 | 56 | 941.0 | 56.1 | 2.44 |
| 30 | 4.31 | 2610 | 34.14 | 32.0 | 30 | 120 | 80 | 658.7 | 64.7 | 3.07 |

What is claimed is:

1. A catalyst for the polymerization of olefins comprising the reaction product between:

(A) a metallocene compound of formula (I), $$(YR_p)_q(CP)(CP')MX'_2 \qquad (I)$$

wherein Cp is a group selected from the group consisting of groups of formula (II):

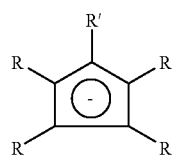

and (III):

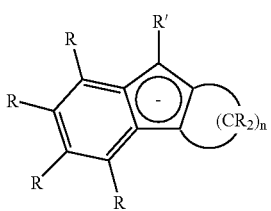

Cp' is a group selected from the group consisting groups of formula (II), (III), and (IV):

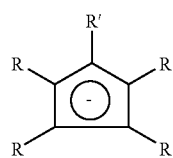

wherein n and m, the same or different from each other, are integers from 2 to 6 inclusive, the R substituents, the same or different from each other, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals, $C_7$–$C_{20}$ arylalkyl radicals, wherein two adjacent R substituents may form a $C_5$–$C_8$ cycle, the R' substituents being defined in the same way as the R substituents or as a group capable of forming part of the divalent bridging group of formula $(YR_p)_q$, Y being selected from the group consisting of C, Si, Ge, N or P, p being 1 when Y is N or P, and p being 2 when Y is C, Si, or Ge, q being selected from 0, 1, 2, or 3, M is a transition metal selected from the group consisting of Ti, Zr or Hf, and the X' substituents, the same or different from each other, are selected from the group consisting of halogen atoms, —OH, —SH, —R, —OR, —SR, —NR$_2$, or PR$_2$, R having the meaning given above, (B) an aluminoxane or one or more compounds capable of forming an alkyl metallocene cation.

2. A catalyst according to claim 1, wherein the metallocene compound of formula (I) is selected from dimethylsilanediyl-bis (2, 3-cyclotetramethyleneinden-1-yl) zirconium dichloride, dimethylsilanediyl-bis (octahydrofluorenyl) zirconium dichloride, isopropyliden(cyclopentadienyl)(2, 3-cyclotetramethyleneinden-1-yl) zirconium dichloride, and isopropyliden(cyclopentadienyl)(2, 3-cyclotetramethyleneinden-1-yl) hafnium dichloride.

3. The catalyst according to claim 1, wherein the alumoxane is selected from methylalumoxane and isobutylalumoxane.

4. A process for the polymerization of olefins comprising the polymerization reaction of at least one olefinic monomer in the presence of the catalyst of claim 1.

5. The process according to claim 4, wherein ethylene is copolymerized with at least one higher olefin.

6. The process according to claim 4, wherein the product is an LLDPE copolymer.

7. The process according to claim 4, wherein the product is an elastomeric copolymer of ethylene with alpha-olefins of the formula CH$_2$=CHR, wherein R is an alkyl radical having from 1 to 10 carbon atoms.

8. The process according to claim 7, wherein the product is an elastomeric copolymer of ethylene with alpha-olefins of the formula CH$_2$=CHR, wherein R is an alkyl radical having from 1 to 10 carbon atoms, and wherein the product further contains a small proportion of units deriving from polyenes.

9. The process according the claim 8, wherein the proportion of units deriving from polyenes is from 0.1 to 20% by weight.

10. A process for the oligomerization of propylene, the process comprising oligomerizing propylene in the presence of the catalyst of claim 1.

* * * * *